(12) United States Patent
Syfrig

(10) Patent No.: US 8,177,555 B2
(45) Date of Patent: May 15, 2012

(54) DEVICE FOR EXTRACTING A TOOTH ROOT

(76) Inventor: Benno Syfrig, Lucerne (CH)

( * ) Notice: Subject to any disclaimer, the term of this patent is extended or adjusted under 35 U.S.C. 154(b) by 66 days.

(21) Appl. No.: 12/444,164

(22) PCT Filed: Oct. 4, 2007

(86) PCT No.: PCT/EP2007/008618
§ 371 (c)(1),
(2), (4) Date: Oct. 15, 2009

(87) PCT Pub. No.: WO2008/043479
PCT Pub. Date: Apr. 17, 2008

(65) Prior Publication Data
US 2010/0047739 A1 Feb. 25, 2010

(30) Foreign Application Priority Data
Oct. 6, 2006 (CH) .................................. 1599/2006

(51) Int. Cl.
*A61C 3/08* (2006.01)
(52) U.S. Cl. ......................................... 433/151; 433/152
(58) Field of Classification Search .................. 433/121, 433/141, 150–152, 158–162, 229
See application file for complete search history.

(56) References Cited

U.S. PATENT DOCUMENTS

| | | | | |
|---|---|---|---|---|
| 5,865 A * | 10/1848 | Dubs | .............................. | 433/152 |
| 723,710 A * | 3/1903 | McCune | ....................... | 433/147 |
| 772,324 A * | 10/1904 | Asdell | ............................ | 433/152 |
| 858,914 A * | 7/1907 | Shannon | ........................ | 433/151 |
| 927,420 A * | 7/1909 | Lyle | ................................ | 433/151 |
| 1,094,269 A * | 4/1914 | Taylor | ............................ | 433/154 |
| 2,210,349 A * | 8/1940 | Van Beeck | ..................... | 433/152 |
| 2,640,266 A * | 6/1953 | Sarti | ............................. | 433/152 |
| 2,776,490 A * | 1/1957 | Carfagni | ....................... | 433/151 |
| 3,494,035 A * | 2/1970 | Everett et al. | ................. | 433/121 |
| 3,686,756 A * | 8/1972 | Pankratz | ....................... | 433/151 |
| 3,702,028 A * | 11/1972 | Edelman | ....................... | 433/150 |
| 4,300,885 A * | 11/1981 | Khait | ............................ | 433/151 |
| 4,443,196 A * | 4/1984 | Rico | ............................. | 433/158 |
| 5,217,371 A * | 6/1993 | Lukase et al. | ................. | 433/150 |
| 5,545,038 A * | 8/1996 | Beebe | ............................ | 433/120 |
| 5,839,896 A * | 11/1998 | Hickok et al. | ................. | 433/159 |
| 6,019,602 A * | 2/2000 | Fletcher et al. | ............... | 433/152 |
| 7,303,395 B2 * | 12/2007 | Hornig et al. | ................. | 433/159 |
| 7,435,087 B2 * | 10/2008 | Syfrig | ............................ | 433/152 |
| 2004/0126741 A1 * | 7/2004 | Hornig et al. | ................. | 433/152 |
| 2007/0218423 A1 * | 9/2007 | Sapian | .......................... | 433/152 |
| 2008/0090206 A1 * | 4/2008 | Hoke et al. | ..................... | 433/152 |

FOREIGN PATENT DOCUMENTS

DE 4318253 A1 * 12/1994
DE 202006001276 U1 * 4/2006

* cited by examiner

*Primary Examiner* — Cris L Rodriguez
*Assistant Examiner* — Hao D Mai
(74) *Attorney, Agent, or Firm* — Brian Roffe

(57) ABSTRACT

The invention relates to a device (1) for extracting a tooth root, said device having a pin (2) which can be inserted and fixed in the tooth root (10). The pin (2) can be fixed to the front end of a unit (5) via a connection piece (3). The unit (5) can transfer an impact force to the pin (2) in the direction of extraction (A). The device enables an especially simple operation, without clearance problems or danger of injury in the mouth area, particularly on account of the good access to the tooth root provided by the connection piece, which is designed as a thin connection rod.

4 Claims, 2 Drawing Sheets

DEVICE FOR EXTRACTING A TOOTH ROOT

FIELD OF THE INVENTION

The invention relates to a device for extraction of a dental root having a pin that can be inserted into the dental root and secured there and having a unit that can be connected to the pin for generating force required for extraction of the root, and wherein the pin can be secured on a distal end of the unit by a connecting piece, whereby an impact force that can be transmitted to the pin in a direction of extraction can be generated by the unit.

BACKGROUND OF THE INVENTION

A device of this type is known from WO 2004/060191. It comprises a pin that can be inserted into the dental root and secured there, preferably a threaded pin that can be screwed into the dental root and can be connected by a tension element, e.g., a cable to a tension unit. The tensile force required for extraction of the root is generated by the manually operable chucking device.

OBJECTS AND SUMMARY OF THE INVENTION

The object of the present invention is to improve upon a generic device for the extraction of dental roots, such that effective extraction forces can be generated with it in a simple design.

This object is achieved according to the invention by a device for extraction of a dental root, having a pin that can be inserted into the dental root and secured there and having a unit that can be connected to the pin for generating force required for extraction of the root. The pin can be secured on a distal end of the unit by a connecting piece, whereby an impact force that can be transmitted to the pin in a direction of extraction can be generated by the unit. Further, the pin is a threaded pin having threads at a free end region to enable the pin to be screwed into the dental root, and the unit has an elongate housing and a striker that is displaceable in an interior of the housing. The striker is displaced in the extraction direction in the interior of the housing to generate the impact force such that impact of the striker against the housing generates the impact force which is transferred to the pin. Impacts of the striker against the housing of the unit are generated mechanically, pneumatically or electromagnetically and triggered manually. The connecting piece is a connecting rod with the pin fastened onto one end region of the connecting rod and which is detachably connectable to the unit at another end region of the connecting rod facing away from the pin. The connecting rod is made of a slightly elastic material and has a small diameter of a few millimeters so that it takes up little space on insertion into the mouth. The pin can be screwed into the dental root and then the unit is manually triggered to cause the mechanical, pneumatic or electromagnetic generation of the impact force which in turn causes extraction of the dental root into which the pin is screwed.

Additional preferred embodiments of the inventive device comprise the subject matter of the dependent claims.

Forces acting on the pin in the extraction direction can be transmitted easily with the inventive device for extraction of dental roots. The device allows especially simple handling and provides good accessibility to the dental roots without problems of clearance or a risk of injury in the oral area thanks to the connecting piece, which is designed as a thin connecting rod.

BRIEF DESCRIPTION OF THE DRAWINGS

The invention is explained in greater detail below on the basis of the drawing, in which.

DETAILED DESCRIPTION OF THE INVENTION

Figure 1:
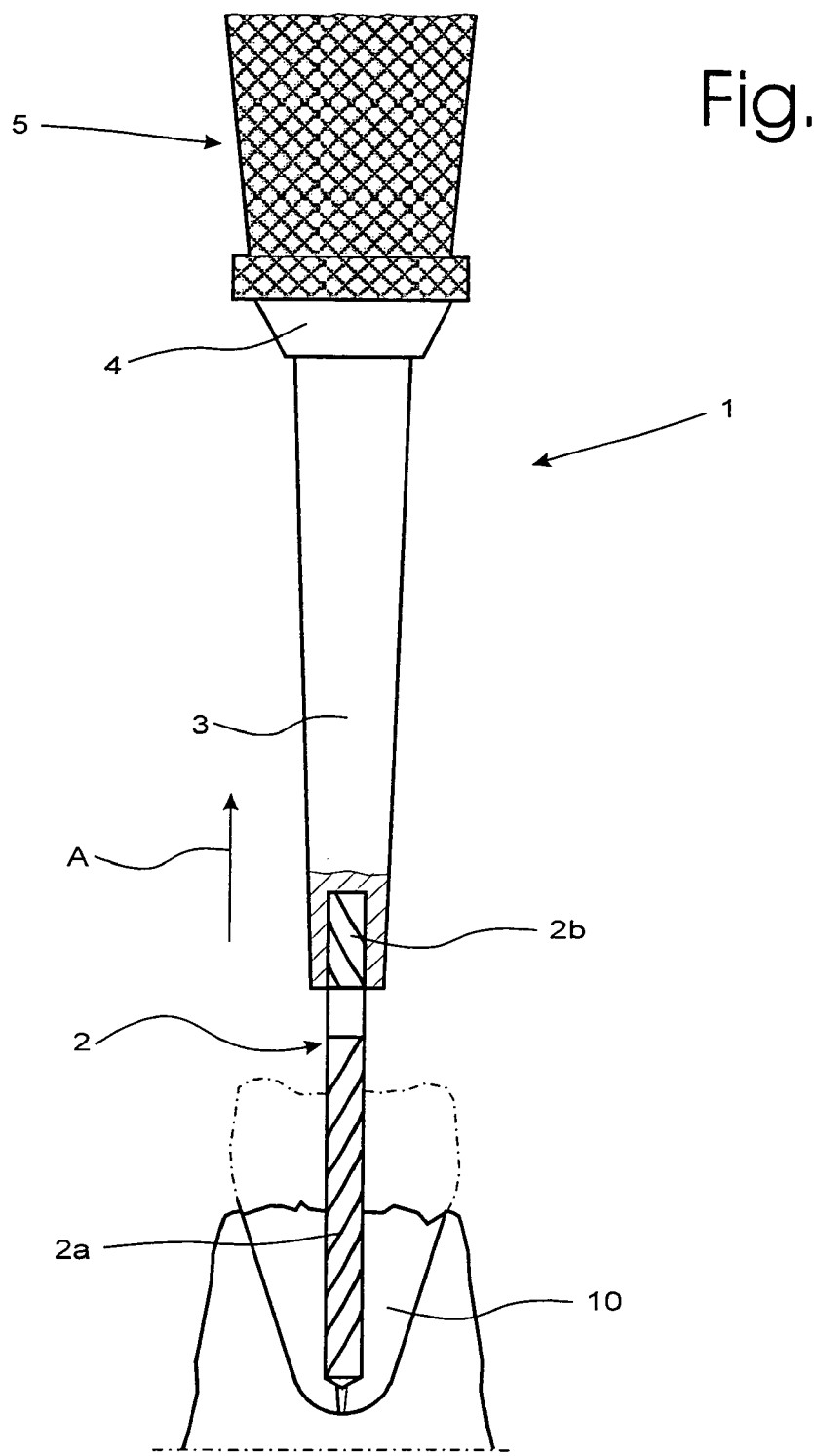
FIG. 1 shows schematically a pin screwed into a dental root, connected by a connecting rod to a unit for generating forces acting in the direction of extraction.

FIG. 1 shows a device 1 for extraction of dental roots 10 illustrated schematically, said device comprising a pin 2 that is inserted into the dental root and is secured there, said pin having been applied by a connecting piece 3 on the distal end 4 of a unit 5 for generating the force required for extraction of a root.

The pin 2 is designed as a threaded pin and is screwed into the dental root 10 (via threaded portion with screws 2a) and/or into a borehole prepared therein. The connecting piece 3 is permanently or detachably connected to the pin 2. The connecting rod 3 is detachably connected to the unit 5, e.g., by screw connection (via threaded portion with screws 2b), on the end facing away from the pin 2. Forces acting in the direction of extraction and transmitted to the pin 2 by a part receiving the forces by way of the connecting rod 3 can be generated with this unit 5.

The extraction forces may be generated mechanically, pneumatically or electromagnetically. They are triggered by hand, so to speak, by pushing a button and are executed individually or repeatedly.

Figure 2:
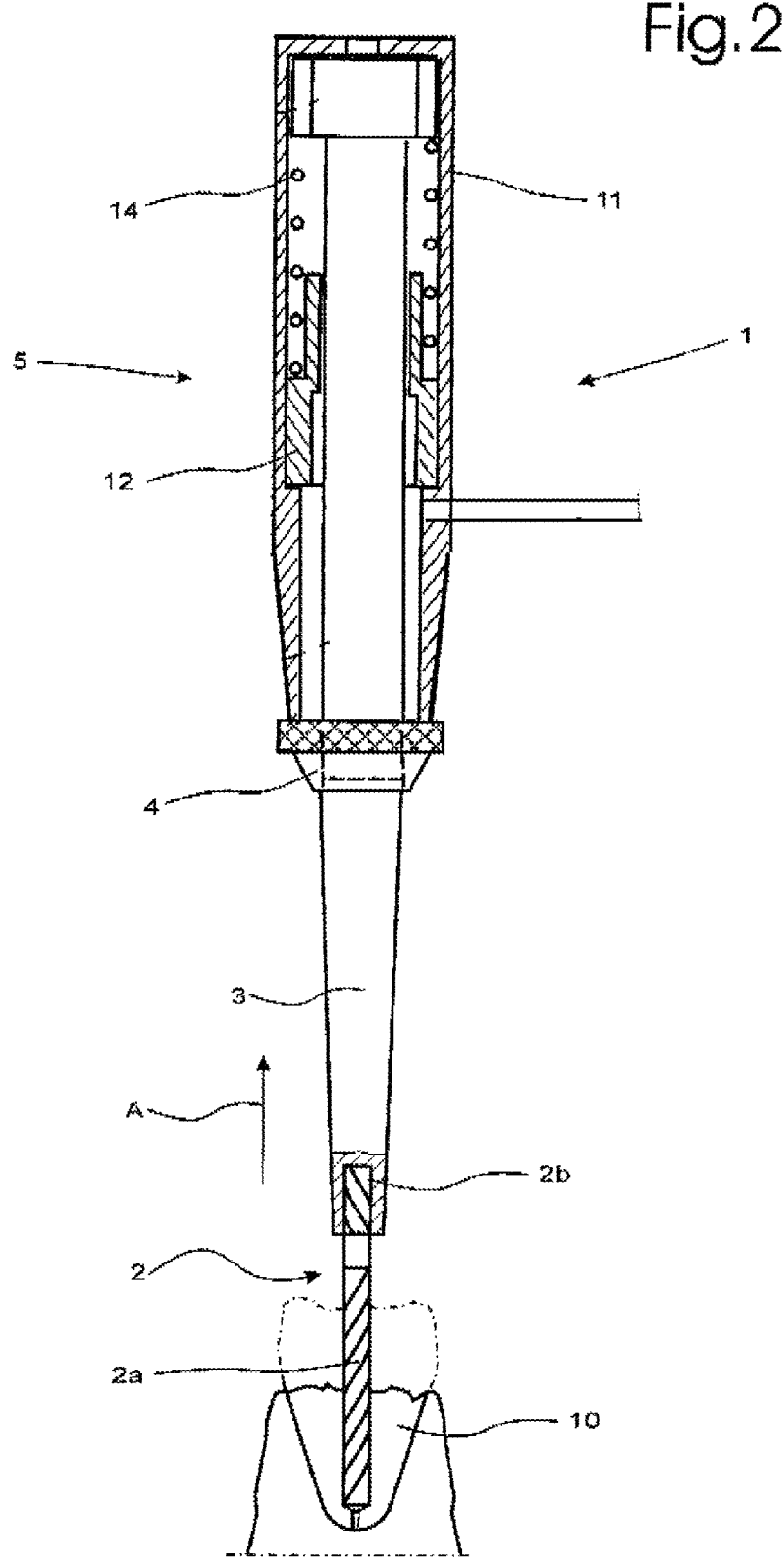
FIG. 2 is a view of the unit of DE 43 18 253 included as part of the dental root extraction device in accordance with the invention.

The unit 5 may correspond in design and function to an essentially known crown extraction device such as that known from DE 43 18 253, for example (see FIG. 2 wherein the unit 5 includes a housing 11, a striker 12 displaceable in the housing and a spring 14), which is incorporated by reference herein. With this crown extraction device, the pneumatically operable striker mechanism is displaceably movable on a rod, on whose proximal end is placed an end piece that receives the impact, said rod being provided with a gripping device for the crown to be extracted. Impacts are transmitted to the gripping device via the rod. Spring 14 is provided for the respective resetting of the striker 12 distally in the direction toward the pin 2.

The connecting rod 3 is preferably made of a material having a low elasticity, e.g., hard rubber, which provides a certain flexibility during use. Furthermore, it is advantageously provided with a small diameter of a few millimeters, so that it takes up little space on insertion into the mouth because it is situated approximately on an axis to the central axis of the dental root 10 and to the pin 2. The end of the connecting rod in the unit 5 is of course outside of the mouth.

It would also be conceivable for the pin 2 as well as the connecting rod 3 to be designed in one piece and for the connecting rod 3, which is permanently attached to the pin 2 screwed into the dental root, to be connected to the unit part transmitting the impacts.

The inventive device for extraction of dental roots allows especially simple handling and, thanks to the connecting piece designed as a thin connecting rod in particular, it allows also good accessibility to the dental roots without any problems of space or risk of injury in the oral area.

This impact-like extraction force could essentially be generated by a means other than a striker mechanism.

The invention claimed is:

1. A device for extraction of a dental root, having a pin that can be inserted into the dental root and secured there and having a unit that can be connected to the pin for generating force required for extraction of the root, the pin can be secured on a distal end of the unit by a connecting piece, whereby an impact force that can be transmitted to the pin in a direction of extraction can be generated by the unit, wherein:

the pin is a threaded pin having threads at a free end region to enable the pin to be screwed into the dental root;

the unit has an elongate housing and a striker that is displaceable in an interior of the housing, the striker being displaced in the extraction direction in the interior of the housing to generate the impact force such that impact of the striker against the housing generates the impact force which is transferred to the pin, impacts of the striker against the housing of the unit are generated mechanically, pneumatically or electromagnetically and triggered manually, the connecting piece is a connecting rod with the pin fastened onto one end region of the connecting rod and which is detachably connectable to the unit at another end region of the connecting rod facing away from the pin, wherein the connecting rod is made of a slightly elastic material, wherein the connecting rod has a small diameter of a few millimeters so that it takes up little space on insertion into the mouth, whereby the pin is screwed into the dental root and then the unit is manually triggered to cause the mechanical, pneumatic or electromagnetic generation of the impact force which in turn causes extraction of the dental root into which the pin is screwed.

2. The device according to claim 1, wherein a spring is provided for resetting of the striker distally in a direction toward the pin.

3. The device according to claim 1, wherein the connecting rod is connected to the unit by screw connection.

4. The device according to claim 1, wherein the connecting rod is manufactured from hard rubber.

* * * * *